(12) United States Patent
Roberts et al.

(10) Patent No.: US 9,505,698 B2
(45) Date of Patent: Nov. 29, 2016

(54) PROCESS FOR RECOVERING WATER, METAL AND ORGANICS FROM THE PRODUCTION OF POLYCARBOXYLIC ACID

(71) Applicant: Johnson Matthey Davy Technologies Limited, London (GB)

(72) Inventors: Simon Roberts, Stockton-on-Tees (GB); Julian Stuart Gray, London (GB)

(73) Assignee: Johnson Matthey Davy Technologies Limited (GB)

( * ) Notice: Subject to any disclaimer, the term of this patent is extended or adjusted under 35 U.S.C. 154(b) by 0 days.

(21) Appl. No.: 14/911,045

(22) PCT Filed: Jul. 31, 2014

(86) PCT No.: PCT/GB2014/052361
§ 371 (c)(1),
(2) Date: Feb. 9, 2016

(87) PCT Pub. No.: WO2015/022493
PCT Pub. Date: Feb. 19, 2015

(65) Prior Publication Data
US 2016/0200658 A1 Jul. 14, 2016

(30) Foreign Application Priority Data
Aug. 14, 2013 (GB) .................. 1314561.0

(51) Int. Cl.
| | | |
|---|---|---|
| C07C 51/43 | (2006.01) |
| C07C 51/487 | (2006.01) |
| B01D 61/24 | (2006.01) |
| B01D 61/58 | (2006.01) |
| C07C 51/16 | (2006.01) |
| C07C 51/47 | (2006.01) |
| C07C 51/42 | (2006.01) |

(52) U.S. Cl.
CPC ............ *C07C 51/487* (2013.01); *B01D 61/243* (2013.01); *B01D 61/58* (2013.01); *C07C 51/16* (2013.01); *C07C 51/42* (2013.01); *C07C 51/43* (2013.01); *C07C 51/47* (2013.01); *B01D 2311/263* (2013.01); *B01D 2311/2673* (2013.01)

(58) Field of Classification Search
CPC .............................. C07C 51/43; C07C 51/457
USPC ........................................................ 562/487
See application file for complete search history.

(56) References Cited

FOREIGN PATENT DOCUMENTS

WO 2010/032263 A2 3/2010
WO 2010/122304 A1 10/2010

OTHER PUBLICATIONS

International Search Report and Written Opinion for PCT/GB2014/052361 dated Nov. 28, 2014.

*Primary Examiner* — Sikarl Witherspoon
(74) *Attorney, Agent, or Firm* — Armstrong Teasdale LLP

(57) ABSTRACT

In a process for recovering water, metals, soluble organics and insoluble organics from a process for the production of a polycarboxylic acid, the stream is cooled to a temperature at which dissolved organics precipitate. The precipitate organics are separated from a liquid stream and recycled to the production process. The liquid stream is then treated with an alkali to convert remaining organics to the alkali salt form and the metals present to be converted to an insoluble form. The insoluble metals are recovered from a liquid stream and this liquid stream, with the alkali salts of the organics, is passed to a membrane separation unit where it is separated into a permeate comprising water and a retentate comprising water and alkali organic salts. The permeate is recovered and recycled to the production process. The retentate also is recovered.

15 Claims, 4 Drawing Sheets

PROCESS FOR RECOVERING WATER, METAL AND ORGANICS FROM THE PRODUCTION OF POLYCARBOXYLIC ACID

The present invention relates to a process for the treatment of effluent streams from the production of aromatic polycarboxylic acids. More specifically, the invention relates to a process for the treatment of effluent streams from the production of terephthalic acid or isophthalic acid.

Typically crude terephthalic acid is produced by the oxidation of p-xylene. The oxidation is generally conducted using acetic acid as solvent in the presence of a catalyst. The solution is then cooled in a stepwise manner to crystallise the terephthalic acid. The terephthalic acid crystals must then be removed from the acetic acid solvent and this is commonly carried out by separation such as by the use of centrifuges or filters. The removed crystals are then subjected to a drying step to remove residual moisture. The crude terephthalic acid is not generally of sufficient quality for use in the production of polyester products and it may then be subjected to a purification process.

In the purification process, in this process, the crude terephthalic acid is slurried with high purity water, generally demineralised water. This slurry is then heated to fully dissolve all the organics to make a solution which is then subjected to hydrogenation in a hydrogenation reactor containing a suitable catalyst. The main intermediate impurity in the crude terephthalic acid is 4-carboxybenzaldehyde. In the hydrogenation reactor, this is hydrogenated to another reaction intermediate known as para-toluic acid. After hydrogenation, the solution is then passed through a series of crystallisers in which the purified terephthalic acid is crystallised while the p-toluic acid remains in solution. The terephthalic acid crystals are then recovered by separation, such as by the use of centrifuges, pressure filters and the like. Water containing organics such as p-toluic acid, any dissolved terephthalic acid and catalyst metals will be recovered from the separation process.

Isophthalic acid is produced by a similar method in which meta-xylene is subjected to oxidation in the presence of a catalyst. The remainder of the process for separation and purification is similar to that described above in connection with terephthalic acid.

Other aromatic carboxylic acids will also be treated in a similar manner. For ease of reference the discussion of prior art processes and the present invention will be with particular reference to terephthalic acid but it will be understood that the comments apply equally to other aromatic carboxylic acids including isophthalic acid.

When the crystals of the product aromatic carboxylic acid are separated, what is left is generally known as the "mother liquor" or "mother liquid". The term "mother liquor" should therefore be construed accordingly. The mother liquor constitutes the main effluent stream in terms of volume from the aromatic polycarboxylic acid production process. This stream comprises the water, which is generally demineralised water, which has been used in the purification section of the production plant together with catalyst metals, so-called "corrosion metals", and organics.

The catalyst metals present will depend on the catalyst used in the reaction process. For the production of terephthalic acid or isophthalic acid the catalyst metals may include cobalt and manganese. The "corrosion metals" may include iron, nickel and chromium. These metals are those which come from corrosion of the vessels etc. in which the production process occurs.

The organics present in the mother liquor fall into two categories, dissolved organics and suspended organic solids. The amount of organics which are in the dissolved phase will be dependent on the solubility of the particular organic at the temperature of the mother liquor as it leaves the separation stage. The amount of organics which will be present in the form of suspended solids depends on the efficiency of the separation device used to remove the desired product. Suitable separation means include multiple stages of centrifuges or filtration means such as rotary pressure filters or rotary vacuum filters. Whatever technology is used for the separation, it will be understood that the separation system is unlikely to be completely efficient and so some slippage occurs at this primary separation stage so that some suspended solids slip through with the mother liquor.

Any loss in the materials used to create polycarboxylic acids represents a financial loss to the process and also a loss in process efficiency. In order to make the process economic it is important that every effort is made to recover as much of the organics from the process as possible. Further, the presence of organics in the mother liquor can have deleterious effects on the environment if retained in the effluent and as such the removal of the organics it is important to minimise the environmental impact.

One example of a process for the treatment of a mother liquor stream is described in WO2010/122304. In this process, the mother liquor stream is cooled to about 40 to 50° C. such that much of the remaining dissolved organics precipitate. These precipitated organics, and any remaining suspended solids, may then be recovered by a secondary filtration stage and returned upstream to the oxidation section of the plant. This secondary separation is often referred to as a mother liquor filter or mother liquid filter.

As the amount of solid to be recovered in this secondary separation is significantly less than that recovered in the primary separation, a higher efficiency filter can be used. Examples of higher efficiency filters include candle filters.

The resulting filtrate stream from the secondary separation comprises primarily water that is saturated with the remaining dissolved organics including unreacted intermediate materials and products. Whilst some suspended solids may remain, the amount of these will generally be negligible.

Conventionally this stream is then sent to an effluent treatment plant. This plant has to be large enough to handle the large volumetric flow rate of the effluent. The filtrate stream may be treated biologically before being discharged into the environment. The discharge may be into a river or ocean or it may be used elsewhere for irrigation purposes. Cleaning the effluent in this way minimises the biological impact on the environment. However, it still represents a loss of overall efficiency as the organics in the mother liquor, which are derived from the expensive feedstock, are destroyed by the biological activity and there is therefore no opportunity to recover them back to the process.

Historically, the volume of water required in the production of these polycarboxylic acids, particularly terephthalic acid or isophthalic acid, is considerable. This can place a significant strain on the available water resources. Therefore it is desirable to construct plants in areas where large volumes of water are available and hence suitable locations for plants can be restricted.

Further, it is necessary that the available water is of a sufficiently high quality to be usable. In some situations it may be necessary to treat the water before it is used in order to obtain the desired level of purity.

In one example, a terephthalic acid product plant was constructed in Taiwan. The area suffered from drought and the water quality was poor. It was therefore suggested that a water recovery system should be used in which treated waste water from the effluent treatment plant is returned as the feed to the water recovery unit.

In the proposed process, the mother liquor was initially treated in an effluent treatment plant and subsequently cleaned in various stages including disinfection followed by increasingly fine levels of filtration, and sterilisation before the stream was in a suitable condition to be fed to a reverse osmosis membrane unit where a portion of the water could be recovered. The organics remaining after the filtration stage were biologically treated in the effluent treatment plant and thus were lost from the process. The recovered water could then be further treated in a demineralised water production unit to obtain the desired level of purification. Whilst this process enables the water to be recycled, it is high in capital and operating costs as the system has to be able to handle the full volumetric flow.

An alternative process is described in EP 164402. This process relates to treating the wash water, which it will be understood is the mother liquor, from the process for manufacturing terephthalic acid. The wash water is first cooled to less than 60° C. to precipitate as much of the organics as possible. The precipitated organics can then be removed by filtration before the stream is passed through a bed of a cation exchange resin to remove the metal catalyst and then through a bed of an anion resin to remove dissolved organics. The treated water can then be returned to the manufacturing process.

It is necessary to have the cooling to precipitate a substantial part of the organics since the organics components are very fouling and if not removed would quickly block the filter or the ion exchange beds. However, the strict temperature control can be difficult to maintain particularly in a batch operation of the kind required for the ion exchange beds. If the temperature is too high, the resin will be damaged and if it is too low, further precipitation can occur which will result in blockage of the beds.

A further problem with the ion exchange resin process is that the resins only have a finite capacity to remove the catalyst ions and the organics. Once the resin is exhausted, it will need to be regenerated. This requires the use of chemicals. Further storage tanks and pumps have to be provided to handle the regeneration chemicals and the resin washings. It will be understood that this increases the cost and complexity of the system to be installed and operated.

A further problem is that the process of EP 164402 requires the use of a strong acid, such as hydrobromic acid, to regenerate the cation exchange resin. It is suggested that the hydrobromic acid can be returned to the oxidation process with the received catalyst metals. However, as discussed in US2003/0078451, the hydrobromic acid is highly corrosive. This creates its own handling problems. Further, the presence of the acid in too high a concentration can lead to increased corrosion within the oxidation section of the plant. Thus the use of the ion exchange process is not preferred.

An alternative process for the recovery of catalyst and organics from a terephthalic acid mother liquor stream is described in U.S. Pat. No. 7,314,954. The stream is passed through an anion exchange resin and is then delivered to a reverse osmosis water treatment system before being returned to the purification section of the plant. The stream is saturated with organics which are only slightly soluble in the aqueous stream. It is therefore suggested that the temperature of the feed is heated by 5 to 10° C. to move the stream away from saturation and to avoid any precipitation in the ion exchange resin. However, the temperature rise has to be controlled as if the temperature of the stream is too high, the resin will be damaged. One disadvantage of this process is that fouling of the reverse osmosis unit membrane with organic matter can occur as the stream becomes concentrated. The requirement for tight temperature controls required by this process can mean that any upset in the plant operation or slight temperature fluctuations would result in the rapid fouling of the membrane which would then need to be replaced.

A further proposal for treating the mother liquor stream is described in U.S. Pat. No. 6,254,779. In this process, alkali is added to the mother liquor to raise the pH of the stream prior to the organics being subjected to oxidation in either a biological based effluent treatment plant or in a wet air oxidation system. This oxidation of the organics converts them to carbon dioxide, water and (bi)carbonate ions and as such they cannot be recovered and are lost to the system. The resulting waste water stream is free from organics and can be fed to a membrane to separate the stream into a permeate which is recycled to a clean water stream and a retentate which will contain alkali cations and carbonate ions. The retentate may be recycled for use in the alkali addition step.

The alkali addition step is used primarily to prepare the stream for the biological effluent treatment plant where the pH must be within a narrow range that is suitable for the micro-organisms employed in the process. If the pH is outside the desired range, the micro-organisms will die and destruction of the organics will cease. Typically, the desired pH is in the range of 6.5 to 8. pH control is particularly important if an anaerobic type digestion process is used.

A second reason for introducing alkali into the stream is that the cobalt and manganese catalyst metals are converted into the insoluble hydroxide or carbonate form which can then be easily recovered as a precipitate.

A further alternative is set out in WO 01/12302 in which wastewater from a terephthalic acid purification process is treated in a series of discrete purification operations. The stream is first passed through a filter to remove insoluble organics. This filtrate is then passed through an ion exchange resin which captures the metals in the stream. The stream is then delivered to a reverse osmosis membrane system which produces a permeate of clean water and a retentate stream containing the soluble organics. The permeate is returned to the purification process whereas the retentate is delivered to an effluent treatment plant.

Some of the soluble organics are converted into sodium salts. Without wishing to be bound by any theory, it is believed that the ion exchange resin bed is responsible for the synthesis of the sodium salts since sodium ions are released from the resin bed during use. These sodium ions react with the organic acids to form the salts. However, the amount of sodium ions released is directly related to the amount of catalyst and corrosion metal captured in the resin. Since the concentration of the soluble organics is much greater than the concentration of the metal ions in the waste water, there will be insufficient sodium released from the resin to fully neutralise the organic acids. Thus, as the concentration of organic acid in the retentate increases, the solubility limit will eventually be exceeded causing the precipitation of organic acids into the retentate leading to a fouling of the membrane.

Whilst the process of the prior art offers various options for treating the mother liquor, they each suffer from various disadvantages and drawbacks and do not necessarily address each of the components of the mother liquor or enable the components to be recovered for recycling. Further, many processes are constrained by solubility limits and can therefore only recover small amounts of water.

It is therefore desirable provide a process for the treatment of a mother liquor from a carboxylic acid production process which enables a stream of water to be provided which is of sufficient purity to enable it to be reused or discarded without risk to the environment as well as provide recovery of metals and organics from the stream. Additionally or alternatively, it is desirable to provide a process which is efficient and cost effective in both capital and operating costs. It is also desirable to provide a process which does not require the aromatic carboxylic acid plant to be built in regions which have a plentiful water supply or built with full effluent treatment plant to recover both metals and organics from the polycarboxylic acid mother liquor stream.

Thus according to the present invention there is provided a process for recovering water, metals, soluble organics and insoluble organics in a mother liquor stream from the separation stage of a process for the production of a polycarboxylic acid, wherein the process comprises:
  (a) cooling the stream to a temperature at which dissolved organics precipitate;
  (b) separating the precipitated organics from a liquid stream and recycling said organics to the process for the production of the polycarboxylic acid;
  (c) the liquid stream from step (b) is then treated with an alkali to convert remaining organics to the alkali salt form and the metals present to be converted to an insoluble form;
  (d) recovering the insoluble metals from a liquid stream;
  (e) passing the liquid stream from step (d) comprising the alkali salts of the organics to a membrane separation unit where it is separated into a permeate comprising water and a retentate comprising water and alkali organic salts;
  (f) recovering the permeate and recycling same to the process for the production of the polycarboxylic acid; and
  (g) recovering the retentate.

The polycarboxylic acid mother liquor stream is produced from the separation stage of the purification section of the plant and is typically about 140° C. to about 160° C. and a pressure of from about 3.5 to about 6 bara. Any organics dissolved within the stream at this stage will be at their solubility limit associated with the temperature and pressure conditions at which the primary separation was carried out. The dissolved organics include intermediate products and possibly also some final desired product. Fine crystals of the product acids may also be present if they have slipped through the primary separation means.

The cooling of the feed stream in step (a) may be carried out by any suitable means. In one arrangement, the mother liquor stream is depressurised. As the stream is depressurised it will cool. In one arrangement, the flashing of the stream will depressurise it to atmospheric pressure. This will cause the stream to cool to around 100° C. which is the boiling point of the main component, water. As the stream cools some of the organics within the liquid stream will precipitate. Since the solubility of the organics is dependent on the temperature of the polycarboxylic acid mother liquor stream it is important to reduce the temperature as low as possible to maximise the initial recovery of the organic components. Therefore the stream may be further cooled to about 40° C. to about 60° C. This additional cooling may be achieved by any suitable method. Suitable methods include the use of a heat exchanger. Additionally or alternatively the pressure of the mother liquor stream can be further reduced so that the stream undergoes flash cooling under vacuum conditions.

The precipitated solids can then be separated and recovered by any suitable means. It will be understood that the stream may also include previously suspended solids. These too can be separated and recovered by any suitable means. Typically the solids can be removed by a filtration. Any suitable filtration means may be used. Examples of suitable filters include candle filters and rotary pressure filters.

The separated organic solids can then be recycled back to process for producing the polycarboxylic acid. Where the process is for the production of terephthalic acid, the separated organic solids will typically be mixed with acetic acid prior to being returned to the oxidation reaction where any intermediate organics, such as p-toluic acid in the case of the production of terephthalic acid, can be further oxidised to the desired terephthalic acid. By this means, desirable organics are not lost from the process and as such the efficiency and the economics of the process are improved.

Once the precipitated organics are removed, the resulting stream will comprise water, dissolved organics, and dissolved metals.

The liquid from which the precipitated organics are removed is then mixed with an alkali to increase the pH of the stream. In one arrangement, the addition of the alkali may increase the pH to at least 8 and preferably higher.

Any suitable alkali may be used. In one arrangement, sodium hydroxide, sodium carbonate, sodium bicarbonate, potassium hydroxide, calcium hydroxide, or ammonium hydroxide may be used. The addition of the alkali converts the organics dissolved in the stream to their alkali salt form. Thus, for example, p-toluic acid becomes sodium p-toluate and terephthalic acid becomes sodium terephthalate. These compounds have a much greater solubility than their acid counterparts and as such the conversion prevents the precipitation of the organics when the stream is concentrated in the downstream part of the process. Preferably sufficient alkali will be added to convert all of the organics present in the stream to their alkali salt form. This prevents precipitation of the organics in the subsequent membrane separation unit.

The additional of alkali enables the metals present in the stream to be converted to insoluble form which can precipitate from the stream. Where the alkali is sodium hydroxide, sodium carbonate or sodium bicarbonate, the catalyst metals such as cobalt and manganese will be precipitated as, for example, cobalt oxides, cobalt hydroxides, cobalt carbonates, manganese oxides, manganese hydroxides and manganese carbonates. The production of metal salts will occur not only for the catalyst metals but it is anticipated that most, if not all, metals present in the mother liquor stream will be precipitated out of solution. Thus it will be understood that the addition of alkali will enable metals such as iron, nickel and zinc to be precipitated out of the stream. This offers environmental advantages since the final effluent discharge will not include these heavy metals.

The precipitated metals can then be separated from the liquid stream. This can be achieved by any suitable means. Cartridge filters or ultra-filters can be used. In one arrangement a series of filtration means may be used with increasing fineness of filtration means. In one arrangement, a course filtration may be used to remove any remaining precipitated organics, and a finer filtration step to remove precipitated catalyst metals or other fine solids.

Whilst it is anticipated that the recovered metal solids will be rich in the catalyst metals such as cobalt and manganese, it will be appreciated that further refining will generally be required to extract the desired catalyst metals before they are recycled to the oxidation plant.

In one arrangement, sodium carbonate or sodium bicarbonate may be used as the alkali rather than sodium hydroxide since the precipitated metal carbonates can be collected and mixed with acetic acid to from metal acetates which can be readily recycled to the oxidation plant.

In one arrangement, particularly where a carbonate alkali is used, the pH adjustment may be carried out in stages, the first stage comprises an initial pH adjustment to precipitate out the catalyst metals which are recovered by filtration followed by a second stage with a further pH adjustment to precipitate out any remaining metals such as the corrosion metals which can be collected by filtration for disposal.

Once the metal alkali salts have been filtered from the polycarboxylic acid mother liquor stream filtrate, the resulting stream, which will generally be clear, is passed to a membrane separation unit. Within the membrane separation unit, the stream is split into a permeate and a retentate.

The permeate comprises water which is generally of sufficient purity and quality to be recycled to a purification section of the process for production. This offers the benefit that there is no requirement to source large volumes of demineralised water or to provide a separate demineralisation plant. This means that the plant does not need to be constructed close to a significant water source.

By the process of the present invention, it may be possible to recover about 75% or more of the water from the mother liquor stream and recycle it back directly into the purification section of the plant without the water requiring treatment. Thus in one aspect of the present invention, the permeate from the membrane separation unit will comprise about 75% or more of the feed fed to the membrane separation unit. It may therefore be necessary to supply about 25% or less of the water required for the purification part of the process from an external demineralised water source.

The retentate, which has a higher concentration of organics than the feed to the membrane separation unit, may be recycled to the feed to the separation unit. This recirculation enables a high crossflow velocity to be maintained across the membrane surface.

A purge will generally be taken to reduce the build-up of organic salts. This purge can be treated by conventional means for treating effluent before being discharged. It will therefore be understood that the volume to be treated is significantly less than that subjected to effluent treatment in prior art processes. Thus a smaller plant can be used which reduces capital and operating costs and any environmental impact.

In one arrangement, the retentate may be treated to recover the organics.

In one alternative arrangement, the retentate may be heated to evaporate the water. The evaporated water can then be condensed. Since the organics contained in the retentate, such as p-toluic, are in the alkali form they will not boil over with the water and therefore this water is also of sufficient purity for recycling to the purification stage of the production process. Although evaporation is not suitable for use on the whole mother liquor stream because of the high costs due to the energy input required, since the retentate may be as little as 25% of the original stream it may be economical to use evaporation to separate more water. This could increase the amount of water recycled to as much as 95% of the original water content of the mother liquor stream As an alternative to the evaporation treatment of the retentate, a second stage membrane separation unit can be employed. In this arrangement the retentate from the first membrane separation unit may be fed to a second membrane separation unit which will operate in a similar way to the first. The recovered liquid may be recycled together with the permeate from the first membrane separation unit to be recycled. In one alternative, it may be fed back to the first stage membrane separation unit.

The retentate, or the retentate which has been subjected to further water separation of as detailed above, may be treated with an acid to reduce the pH so that the organic salts are converted back into the original organic acids. Since the organics are now present in a higher concentration they will precipitate out of solution and can be recovered using conventional solid-liquid separation means. Suitable acids include hydrochloric acid, acetic acid and hydrobromic acid. The recovered organic solids may be recycled back to the oxidation plant or disposed of.

The remaining aqueous stream contains low levels of alkali metal salts, and trace amounts of organic components. This stream may be disposed of using an effluent treatment plant of a much reduced size compared to the prior art examples. The removal of as much organic component from the retentate as possible is beneficial since this will reduce the demand for biological and/or chemical oxygen in the downstream effluent treatment plant.

Due to the small volume of the residual effluent, techniques such as oxidation based treatment processes as alternatives to biological effluent treatment become economically and technically viable.

It will therefore be understood that the present invention offers a significant number of advantages over the prior art arrangements. The process enables a significant volume of water to be recovered prior to the effluent treatment plant which enables a smaller effluent treatment plant to be used. Thus less land is required for the construction of the effluent treatment plant and it is cheaper to run.

As the water is of a sufficient purity to be recycled directly to the purification stage of the production process, the need for a demineralisation unit is obviated which improves the economics. In addition, the recovery of the organics and their recycling to the oxidation process enables a more efficient and cost effective process to be achieved.

The polycarboxylic acid is preferably terephtahlic acid or isophthalic acid.

The present invention will now be described, by way of example, with reference to the accompanying drawings in which.

It will be understood by those skilled in the art that the drawings are diagrammatic and that further items of equipment such as reflux drums, pumps, vacuum pumps, compressors, gas recycle compressors, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

The process of the present invention will be discussed with reference to the production of terephtahlic acid.

Figure 1:
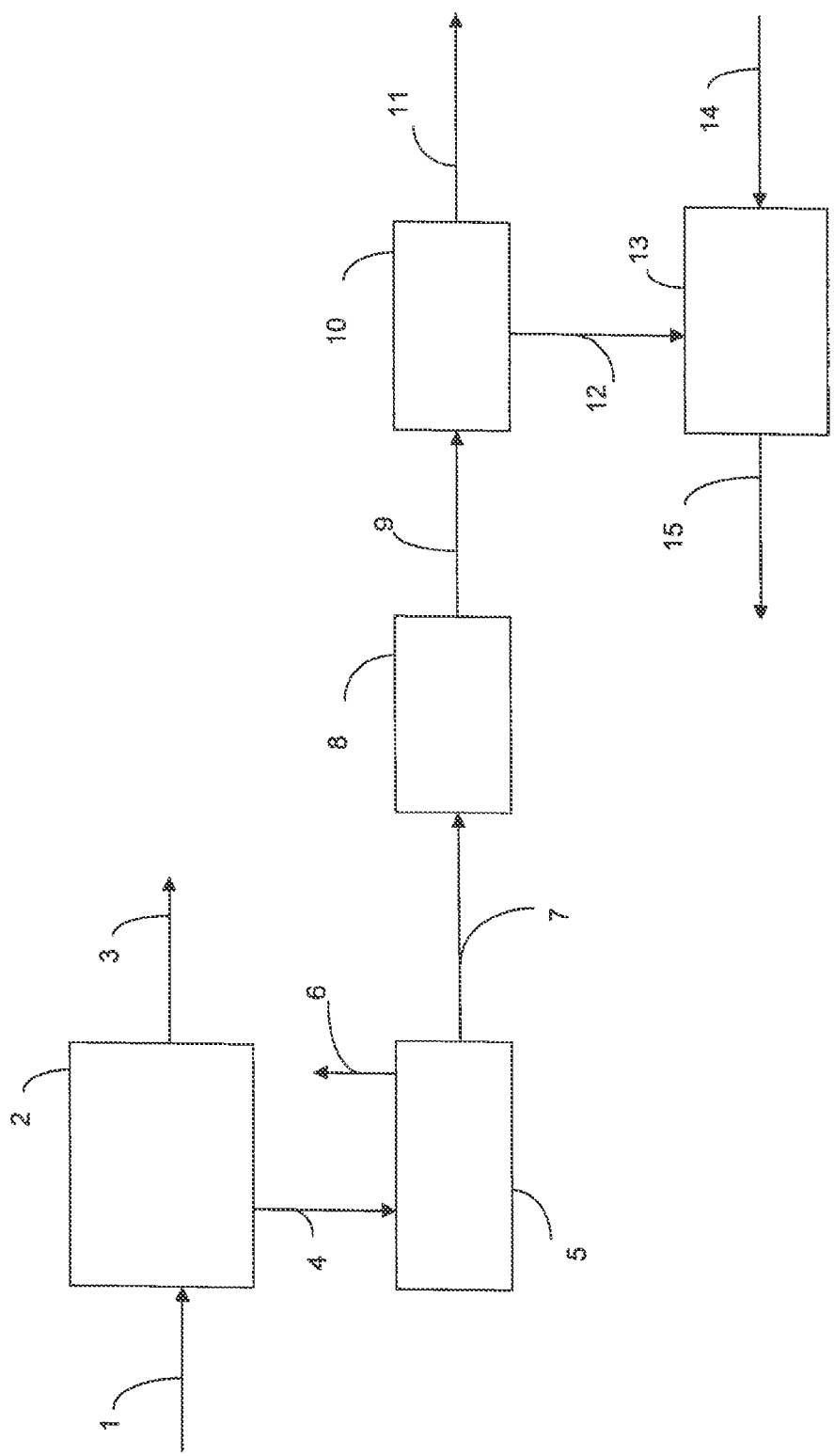
FIG. 1 is a schematic representation of a first part of the separation process of the present invention.
Figure 2:
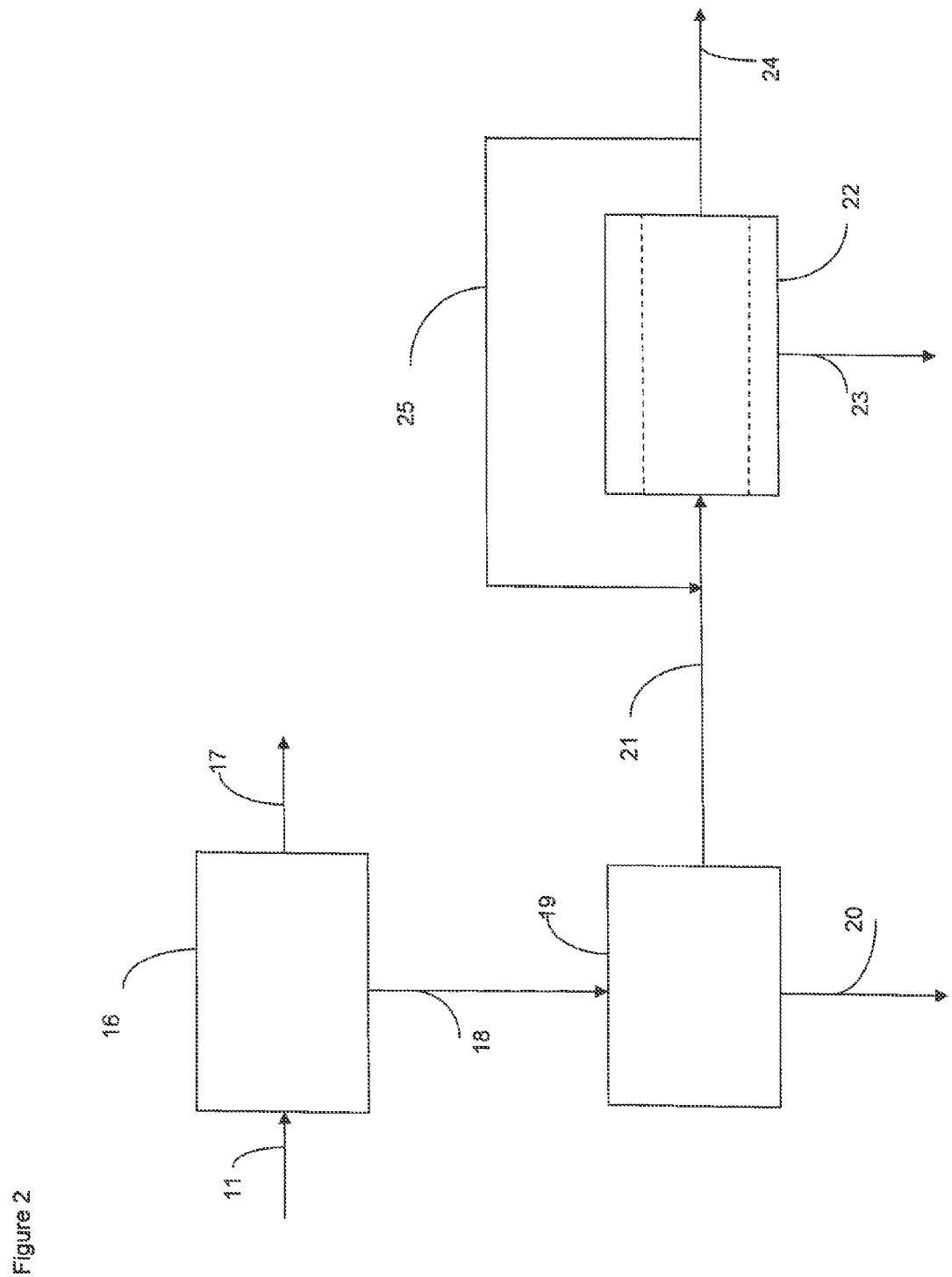
FIG. 2 is a schematic representation of a second part of the separation process of the present invention.

As illustrated in FIG. 1, a slurry of purified terephthalic acid is passed in line 1 to a primary separation unit 2. The separated terephtahlic acid is recovered in line 3 and sent to a dryer (not shown). The mother liquor, at a temperature of from about 140° C. to about 160° C. is passed in line 4 to a flash cooling unit 5 where the liquid stream is cooled and flash steam is released in line 6. The resulting cooled liquid at about 100° C. is fed in line 7 into a further cooling unit 8 where it is cooled to about 40° C. to about 60° C. The cooled stream is passed in line 9 to a secondary separation unit 10 is used to recover terephthalic acid and p-toluic acid that have slipped through the primary separation unit 1 or have precipitated as the cooling has occurred. The recovered organics are sent in line 12 to a reslurry unit 13 where it is mixed with acetic acid solvent fed in line 14 before being returned to in line 15 to the oxidation plant (not shown). The filtrate from the secondary filtration unit 10 is sent in line 11 to the effluent treatment process which is illustrated in FIG. 2.

The filtrate recovered in line 11 from the second filtration unit 10 is passed to an alkali salt formation tank 16 where it contacted with alkali which is introduced in line 17 into the tank 16. The alkali treated stream is then fed in line 18 into a pre-filtration unit 19 in which any catalyst and corrosion metals are recovered and removed in line 20. In one arrangement, further cooling may be incorporated between the tank 16 and the pre-filtration unit 19. The removed metals may be subjected to further treatment.

The alkali is removed in line 21 and passed to a membrane separation unit 22 where it is separated into a permeate and a retentate. The permeate which is water is removed in line 23 for recycling to oxidation and/or the purification part of the production process. The retentate is removed in line 24. The majority of the retentate may be recirculated in line 25 so that it can be fed through the membrane separation unit. The stream in line 24 may be a purge which is passed to effluent treatment or the retentate may be subjected to further treatment.

Figure 3:
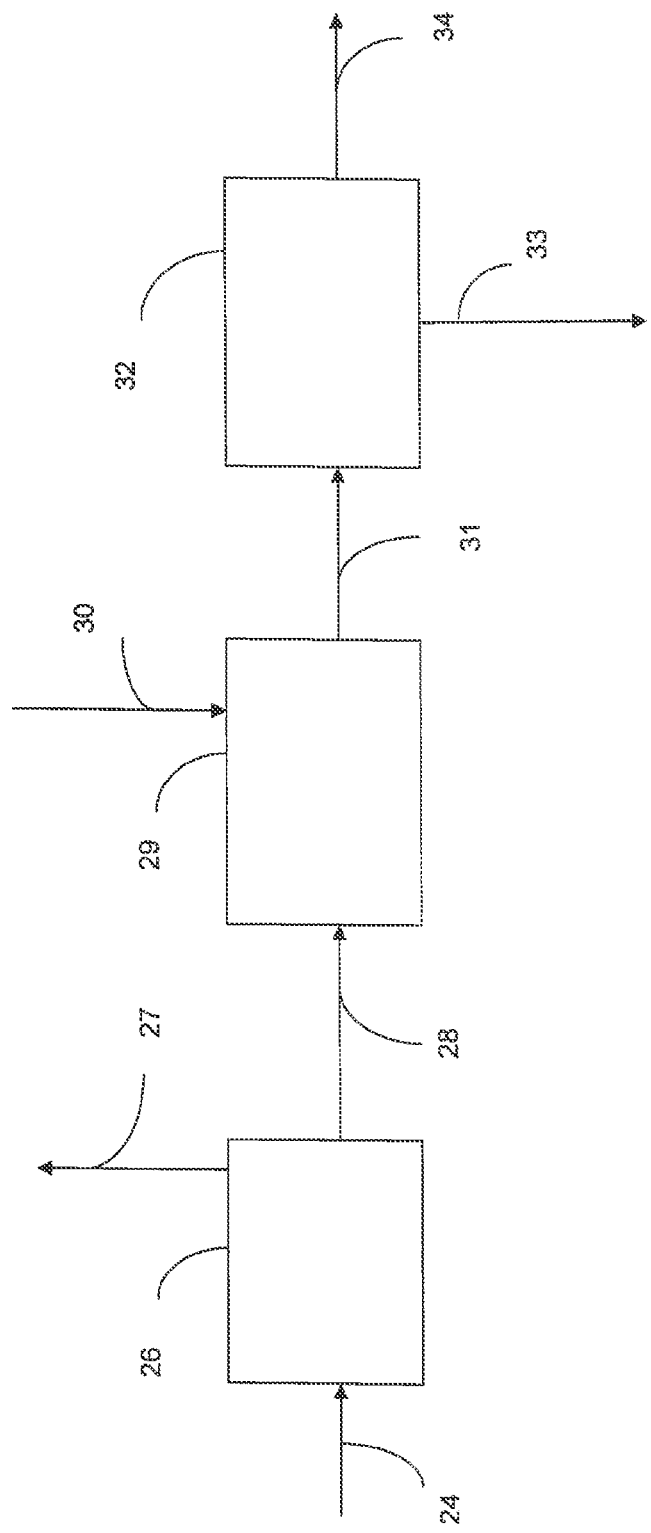
FIG. 3 is a schematic representation of a third part of the separation process of the present invention.

FIG. 3 illustrates one method of retentate treatment. The retentate recovered from the membrane separation unit in line 24 and is delivered to an evaporator 26. Water is evaporated and condensed before being recycled in line 27 to the oxidation or purification process.

The concentrated stream is then passed in line 28 into an acidification unit 29 where it is treated with acid added in line 30. The acidified stream is then fed in line 31 to a filtration unit 32. The recovered organic solids are returned to the oxidation plant in line 33. The residual effluent is removed from the system in line 34 for final effluent treatment.

Figure 4:
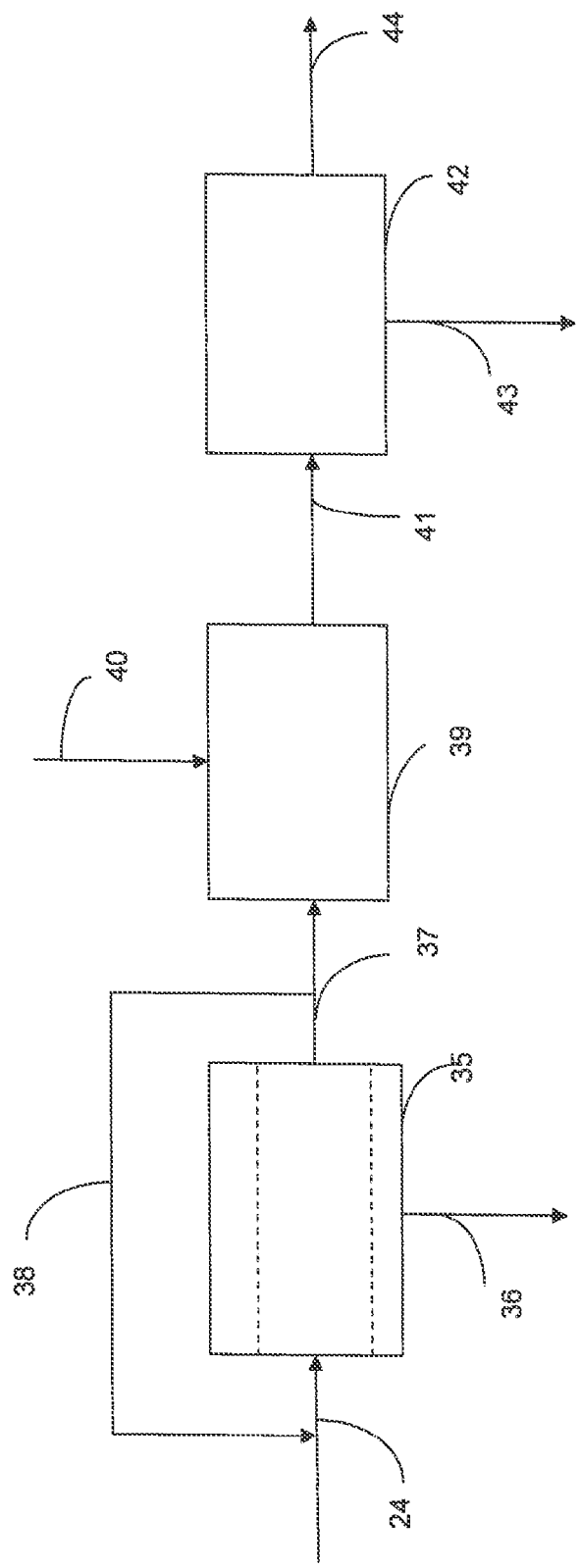
FIG. 4 is a schematic representation of an alternative third part of the separation process of the present invention.

An alternative process for treating the retentate recovered in line 24 is illustrated in FIG. 4. In this process, the retentate is fed in line 24 into a second membrane separation unit 35. The permeate water from the separation unit 25 is returned in line 36 to the production plant or to the first membrane separation unit 22. This may be combined with the streams of lines 21 and 25. The retentate from the second membrane separation unit 22 is removed in line 37. A portion of the retentate can be recirculated around the second membrane 35. The remainder of the retentate in line 37 is fed to the acidification unit 39 where it is mixed with acid added in line 40. The acidified stream is then fed in line 41 into to a filtration unit 42. The recovered solids are removed in line 43 and may be returned to the production process. The effluent is removed in line 44 for further treatment.

The invention will now be further described with reference to the accompanying Examples.

Comparative Example

A feed comprising water and p-toluic acid was added to a BWHR5 membrane operated at 70° C. and 15 barg. No alkali was added to the feed.

It was found that 70% of the water in the feed was recovered in the permeate and 20% of the p-toluic acid had slipped into the permeate. The flux of the membrane was low at a maximum of 40 kg/h·m$^2$ and soon reduced due to fouling of the membrane with a build-up of p-toluic acid.

The results of this test indicate that the quality of the permeate was not sufficient to be returned directly in the terephthalic acid production process nor was the life of the membrane likely to be economic.

Example 1

Sodium hydroxide was added to a feed comprising water and p-toluic acid. The alkali converted the p-toluic acid into sodium p-toluate salt and the pH of the feed to the membrane was maintained at approximately 8.

The acidified feed was passed to a BWHR5 membrane operated at 50° C. and 15 barg. Using a reduced operating temperature was possible since there were no longer any issues relating to the organic's solubility limit as they were now present in the salt form.

Water recovery increased to 80% and p-toluic slip decreased to <5%. Consistent flux levels in the region of 60 to 80 kg/h·m$^2$ were achieved.

The quality of the permeate was suitable for recycle to the terephthalic acid production process.

The invention claimed is:

1. A process for recovering water, metals, soluble organics and insoluble organics in a mother liquor stream from the separation stage of a process for the production of a polycarboxylic acid, wherein the recovering process comprises:
   (a) cooling the stream to a temperature at which dissolved organics precipitate;
   (b) separating the precipitated organics from a liquid stream and recycling said organics to the process for the production of the polycarboxylic acid;
   (c) treating the liquid stream from step (b) with an alkali to convert remaining organics to the alkali salt form and the metals present to be converted to an insoluble form;
   (d) recovering the insoluble metals from a liquid stream;
   (e) passing the liquid stream from step (d) comprising the alkali salts of the organics to a membrane separation unit where it is separated into a permeate comprising water and a retentate comprising water and alkali organic salts;
   (f) recovering the permeate and recycling same to the process for the production of the polycarboxylic acid; and
   (g) recovering the retentate.

2. The process according to claim 1 where in the cooling of the feed stream in step (a) is achieved by depressurising the stream.

3. The process according to claim 1, wherein a second cooling step is conducted.

4. The process according to claim 1, wherein the stream is cooled to about 40° C. to about 60° C.

5. The process according to claim 1, wherein the precipitated solids, optionally with suspended solids, are separated by filtration.

6. The process according to claim 1, wherein the separated organic solids in step (b) are recycled to the process for producing the polycarboxylic acid.

7. The process according to claim 1, wherein treating the liquid stream from step (b) with alkali increases the pH to at least 8.

8. The process according to claim 1 wherein the alkali is at least one of sodium hydroxide, sodium carbonate, sodium bicarbonate, potassium hydroxide, calcium hydroxide, e- and ammonium hydroxide.

9. The process according to claim 1 wherein sufficient alkali is added to convert all of the organics present in the stream to their alkali salt form.

10. The process according to claim 1 wherein the retentate is recycled to the feed liquid stream that is passed to the separation unit.

11. The process according to claim 10 wherein a purge is taken to reduce the build-up of organic salts.

12. The process according to claim 1 wherein the retentate is treated to recover the organics.

13. The process according to claim 1 wherein the retentate is heated to evaporate the water and the water is recycled to the production process.

14. The process according to claim 1 wherein the retentate is passed to a second stage membrane separation unit.

15. The process according to claim 1 wherein the polycarboxylic acid is terephtahlic acid or isophthalic acid.

* * * * *